(12) United States Patent
Kai et al.

(10) Patent No.: US 8,017,706 B2
(45) Date of Patent: Sep. 13, 2011

(54) PROCESS FOR PRODUCTION OF POLYMERS WITH IRON COMPLEX CATALYST

(75) Inventors: Hidetomo Kai, Chiba (JP); Akane Sasamoto, Chiba (JP); Hitoshi Hayakawa, Chiba (JP)

(73) Assignee: DIC Corporation, Tokyo (JP)

( * ) Notice: Subject to any disclaimer, the term of this patent is extended or adjusted under 35 U.S.C. 154(b) by 0 days.

(21) Appl. No.: 12/921,652

(22) PCT Filed: Mar. 10, 2008

(86) PCT No.: PCT/JP2008/054292
§ 371 (c)(1),
(2), (4) Date: Nov. 11, 2010

(87) PCT Pub. No.: WO2009/113148
PCT Pub. Date: Sep. 17, 2009

(65) Prior Publication Data
US 2011/0105703 A1    May 5, 2011

(51) Int. Cl.
C08F 4/70 (2006.01)
C08F 4/80 (2006.01)
C07F 15/02 (2006.01)

(52) U.S. Cl. ............ 526/169.1; 526/169; 526/161; 526/160; 526/142; 526/147; 526/144; 526/69; 526/346; 526/318; 526/318.4; 526/329.7; 526/328; 526/319; 526/303.1; 556/138; 556/144

(58) Field of Classification Search ............ 556/138; 526/169.1
See application file for complete search history.

(56) References Cited

U.S. PATENT DOCUMENTS

| | | | |
|---|---|---|---|
| 6,583,182 B1 * | 6/2003 | Winchell et al. | 514/648 |
| 7,674,866 B2 * | 3/2010 | Nagashima et al. | 526/135 |
| 2009/0118448 A1 * | 5/2009 | Nagashima et al. | 526/135 |

FOREIGN PATENT DOCUMENTS

JP    8-41117 A    2/1996
(Continued)

OTHER PUBLICATIONS

Flassbeck et al., Zeitschrift für Anorganische und Allgemeine Chemie, 1992, 608, 60-68.*

(Continued)

*Primary Examiner* — Rip A. Lee
(74) *Attorney, Agent, or Firm* — McDermott Will & Emery LLP (57) ABSTRACT

The present invention relates to a novel iron complex having a cyclic amine compound as a ligand and a method for producing polymers by polymerizing a radical polymerizable monomer in the presence of the iron complex and a radical generator. The problem for the present invention is providing a method capable of producing a polymer or block copolymer having a chemically convertible functional group at the end from a radical polymerizable monomer and providing a method for recovering the iron complex in a solvent with a high recovery rate after the polymerization reaction. This problem is solved by providing a novel iron complex, a method for producing a polymer in the presence of a radical polymerization initiator that uses the iron complex as a polymerization catalyst and a method for simply and easily recovering the iron complex. The present invention can provide an iron complex useful for the method for producing a polymer by polymerizing a radical polymerizable monomer and a method for producing the polymer using that iron complex.

12 Claims, 2 Drawing Sheets

FOREIGN PATENT DOCUMENTS

| | | |
|---|---|---|
| JP | 2946497 B2 | 9/1999 |
| JP | 2002-80523 A | 3/2002 |
| JP | 2002-356510 A | 12/2002 |
| JP | 2005-105265 A | 4/2005 |
| JP | 2006-257293 A | 9/2006 |
| JP | 2008-100990 A | 5/2008 |
| WO | 2007/032358 A1 | 3/2007 |
| WO | WO 2007/032358 A1 * | 3/2007 |

OTHER PUBLICATIONS

Nagashima et al. JP 2006-257293 (Sep. 2006); abstract and translation in English.*

Wang et al., "Controlled/"Living" Radical Polymerization. Halogen Atom Transfer Radical Polymerization Promoted by a Cu(I)/Cu(II) Redox Process," Macromolecules, 1995, 28, pp. 7901-7910.

Hawker et al., "Initiating Systems for Nitroxide-Mediated "Living" Free Radical Polymerizations: Synthesis and Evaluation," Macromolecules, vol. 29, No. 16, Jul. 29, 1996, pp. 5245-5254.

Chiefari et al., "Living Free-Radical Polymerization by Reversible Addition-Fragmentation Chain Transfer: The RAFT Process," Macromolecules, 1998, 31, pp. 5559-5562.

Matyjaszewski et al., "Atom Transfer Radical Polymerization," Chem. Rev., 2001, 101, pp. 2921-2990.

Uchiike et al., "Evolution of Iron Complexes: Development of Living Radical Polymerization via Ligand Design," Polymer Preprints, Japan, vol. 54, No. 1, 2005, p. 136.

Matyjaszewski et al., "Controlled/"Living" Radical Polymerization of Styrene and Methyl Methacrylate Catalyzed by Iron Complexes," Macromolecules 1997, 30, pp. 8161-8164.

Ando et al., "Iron (II) Chloride Complex for Living Radical Polymerization of Methyl Methacrylate," Macromolecules, vol. 30, No. 16, Aug. 11, 1997, pp. 4507-4510.

Moineau et al., Alternative Atom Transfer Radical Polymerization for MMA Using $FeCl_3$ and AIBN in the Presence of Triphenylphosphine: An Easy Way to Well-Controlled PMMA, Macromolecules, 1998, 31, pp. 545-547.

Teodorescu et al., "Halide Anions as Ligands in Iron-Mediated Atom Transfer Radical Polymerization," Macromolecules, 2000, 33, pp. 2335-2339.

Wieghardt et al., "[{($C_6H_{15}N_3$)Fe}$_2$($\mu$-O) ($\mu$-$CH_3CO_2$)$_2$]2+, a Dinuclear Iron (III) Complex with a Metazidohemerythrin -Type Structure," Angewandte Chemie. International Edition in English, 1983, vol. 22, No. 9, pp. 727.

Flassbeck et al., "Synthesis of N-phenolate-functionalized macrocycles of 1,4,7-triazacyclononane and of 1-oxa-4, 7-diazacyclononane and their cordination chemistry with iron (III)," Zeitschrift fuer Anogranische und Allgemeine Chemie, 1992, vol. 608, pp. 60-68.

* cited by examiner

PROCESS FOR PRODUCTION OF POLYMERS WITH IRON COMPLEX CATALYST

CROSS REFERENCE TO PRIOR APPLICATIONS

This application is a U.S. National Phase application under 35 U.S.C. §371 of International Application No. PCT/JP2008/054292, filed on Mar. 10, 2008. The International Application was published in Japanese on Sep. 17, 2009 as WO 2009/113148 A1 under PCT Article 21(2). The content of the application is hereby incorporated by reference.

TECHNICAL FIELD

The present invention relates to a novel iron complex having a cyclic amine compound as a ligand and a method for producing polymers by polymerizing a radical polymerizable monomer in the presence of the iron complex and a radical generator. More specifically, the present invention uses an iron complex having a cyclic amine compound as a ligand that is usable for a wide range of types and combinations of radical polymerizable monomers and relates to a method for producing a polymer that has a chemically convertible terminal functional group while controlling molecular weight and molecular structure and a method for recovering the iron complex from the polymeric substance.

BACKGROUND

Living radical polymerization, where, unlike conventional radical polymerization, the polymer growth terminus is active so as to be chemically convertible, can freely control the molecular weight, monomer residue order, dimensional structure and the like of the polymer; therefore, it has attracted much attention for the last ten years. Examples include atom transfer radical polymerization (ATRP) (Non-patent Reference 1), nitroxide mediated radical polymerization (NMP) (Non-patent Reference 2) and reversible addition chain transfer (RAFT) radical polymerization mediated by sulfur compounds (Non-patent Reference 3). Among these, atom transfer radical polymerization (ATRP) that uses combinations of metal complexes and halogen compounds shows particular applicability to a wide range of monomer types. Methods that precisely control the polymer using this have spread not only to polymer synthesis, but also to chemical modification of substrate surfaces and interfaces and device construction.

The metal catalysts used in ATRP normally have copper or ruthenium as their central metal. They are not a well-defined metal complex, and they are used after the compounds formed from the metal ions and their ligands (amines for example) are mixed into the polymerization reaction. In such polymerization systems, the metal catalytic activity occurs after the ligands bind in the system and the complex is formed. When the coordinating force of the ligands is not very strong, metal that does not form the complex arises, and this metal cannot show catalytic activity. Therefore, the catalytic efficiency of the metal is reduced, and there is the demerit of having to increase the concentration of the metal or having incompatibility with production of high molecular weight polymers. Increasing the metal concentration places most of the burden on the process for eliminating the metal after the polymerization reaction or gives rise to the possibility of environmental contamination due to metal toxicity. On the other hand, to prevent a decrease in the catalytic efficiency of the metal, an excess of amine ligands (see Patent Reference 1 and 2, for example) may be used. However, if the type or the like of the monomer changes in the polymerization reaction because of the use of an excess of amine ligands, a large number of problems, such as the reaction becoming difficult to control and polymer purification becoming difficult because compounds other than the monomer are mixed in arise.

Typically, an organic compound of an activated halogen is used for the polymerization initiator in ATRP. Replacing the activated halogen compound initiator with a conventional radical generator (for example, a peroxide radical generator or azo radical generator) in the polymerization is called reverse ATRP (R-ATRP). With R-ATRP, a reactive residue may be introduced at the end of the polymer by adding a metal catalyst to the conventional radical polymerization process, thereby making the synthesis of a block copolymer possible. Therefore, R-ATRP is a useful production method for obtaining polymers where the structure is controlled in an existing production process. Most R-ATRP methods basically use copper ion complexes with amines as the ligands. The same problems as those in ATRP, such as increasing in metal ion concentration, increasing ligand concentration, reduction of catalytic efficiency, difficulty in polymer purification and polymer coloration, are involved.

The production of polymers using a safe, inexpensive iron catalyst with living radical polymerization that uses a metal complex has received much attention from the standpoint of being environmentally friendly (Non-patent Reference 4).

With ATRP, polymer production methods that are carried out after mixing iron ions and ligands (amines, phosphines and phosphite ester compounds) with polymerizable monomers and production methods for polymers that are carried out after mixing synthesized iron complexes and polymerizable monomers have been disclosed (Non-patent Reference 5). For example, a methyl methacrylate polymerization method where divalent iron ions and an amine ligand are mixed with a monomer and a halogen initiator is used therein (Non-patent Reference 6) and a methyl methacrylate polymerization method where an iron complex of divalent iron ions and a phosphorous compound ligand are used with a halogen initiator have been reported (for example, Non-patent Reference 7, Patent Reference 3).

There have also been investigations into using environmentally friendly iron ion compounds as catalysts in R-ATRP. For example, methyl methacrylate polymerization using a mixture of $FeCl_3$ and triphenyl phosphine as the catalyst (Non-patent Reference 8) and methacrylate or styrene polymerization using a metal complex formed from organic onium cations and a ferric chloride compound that is anionic as the catalyst (Non-patent Reference 9) have been reported. However, in R-ATRP using these iron complexes or iron ion compounds, there are many problems that should be improved, such as the difficulty of controlling block copolymers.

On the other hand, in living radical polymerization systems that use metal catalysts, there is a large problem with methods for eliminating the metal from the polymer after polymerization. In a certain sense, the elimination of the remaining metal from the polymer is more of a real problem for practical application of living radical polymerization than the polymerization reaction itself. Methods that make use of complexing agents in the purification process have been examined for removing the metal (Patent Reference 4 and 5). The use of environmentally friendly iron ion compounds as catalysts produces no toxicity compared with other metals such as copper, cobalt, ruthenium and the like, and the merits for all of the processes in polymer production, including post-processing and other processes, are great. However, in living radical polymerization that uses iron ions, one can hear about problems in production processes such as the instability of iron catalysts and the difficulty of reusing iron catalysts before problems such as the polymerization efficiency being low.

In a living radical polymerization reaction, the polymerization reaction is carried out using an iron complex with high catalytic activity, and the elimination of that complex from the polymerization reaction and recovery by a simple method without disposing of it is considered to be an extremely important problem.

Patent Reference 1: Published Unexamined Patent Application H08-41117
Patent Reference 2: Published Unexamined Patent Application No. 2002-80523
Patent Reference 3: U.S. Pat. No. 2,946,497
Patent Reference 4: Published Unexamined Patent Application No. 2002-356510
Patent Reference 5: Published Unexamined Patent Application No. 2005-105265
Non-patent Reference 1: J. Wang et al., Macromolecules, Vol. 28, 1995, p. 7901
Non-patent Reference 2: C. J. Hawker, et al., Macromolecules, Vol. 29, 1996, p. 5245
Non-patent Reference 3: Chiefari et al., Macromolecules, Vol. 31, 1998, p. 5559
Non-patent Reference 4: Matyjaszewski et al., Chemical Review, Vol. 101, 2001, p. 2921
Non-patent Reference 5: Sawamoto et al., Polymer preprints, Japan, 2005, vol. 54, No. 2, p. 136
Non-patent Reference 6: Matyjaszewski et al., Macromolecules, Vol. 30, 1997, p. 8161
Non-patent Reference 7: Ando et al., Macromolecules, Vol. 30, 1997, p. 4507
Non-patent Reference 8: G. Moineau et al., Macromolecules, Vol. 31, 1998, p. 545
Non-patent Reference 9: Teodorescu et al., Macromolecules, Vol. 33, 2000, p. 2335

DISCLOSURE OF THE INVENTION

Problems to be Solved by the Invention

The problem to be solved by the present invention is providing a method that can produce a polymer having a functional group that is chemically convertible at the end with quantitative polymerization of a radical polymerizable monomer being possible in a comparatively short time in the presence of a polymerization catalyst system formed of an iron complex having a cyclic amine compound as a ligand and a radical generator. Furthermore, the problem is also providing a method for recovering the metal complex from a solvent with a high recovery rate by simply reprecipitating the polymer in a general purpose solvent after the polymerization reaction.

Means to Solve the Problems

Focus was given to iron complexes that have cyclic amine compounds as ligands for the metal complexes showing catalytic activity in the present invention, and the present invention was completed.

In other words, the present invention provides a novel iron complex given by general formula (1), a production method for a polymer characterized by polymerization of at least one radical polymerizable monomer in the presence of a radical polymerization initiator (Z) using that iron complex (Y) as a catalyst and a production method for a block copolymer characterized by block polymerization of another radical polymerizable monomer after polymerization of that polymer as well as a method for simply and easily recovering the iron complex.

[Formula 1]

(1)

wherein Fe is trivalent, X is a chlorine atom or bromine atom, $R_1$, $R_2$ and $R_3$ are groups selected from hydrogen atoms, alkyl groups with 1 to 12 carbons and benzyl groups that may have substituent groups of 1 to 8 carbons and m and n are integers from 2 to 3, with m and n all being 2 and $R_1$, $R_2$ or $R_3$ all being groups that are methyl groups or ethyl groups being excluded.

Effects of the Invention

By using the iron complex given by general formula (1) above and a radical generator, the polymerization reaction system of the present invention becomes extremely simple and does not need other ligands. Furthermore, because of the superior catalytic activity of the iron complex, the radical polymerization reaction thereof progresses quantitatively. In addition, since an active terminal that is not obtained with normal radical polymerization is formed on the polymer that is obtained, a block copolymer may be produced simply by adding another radical polymerizable monomer after the quantitative polymerization. Furthermore, these iron complexes may easily be recovered by efficient dissolution of the complex in a solvent phase in simple work processes for precipitating the polymer after the polymerization reaction is complete. In other words, the present invention provides many merits for controlling the polymerization reaction in industrial processes by using the iron complex described above in a conventional radical polymerization system.

The effects of the present invention are being able to control environmental contamination more than toxic metal ion systems such as copper complexes by using an iron complex and being able to simplify the post-processing processes for the polymer obtained.

In the present invention, an iron complex (Y) having a halogen and cyclic amine compound coordination is used for the metal complex that is the polymerization catalyst. By combining this with a polymerization initiator and making the polymerization of a radical polymerizable monomer progress using a living radical polymerization form of R-ATRP, the polymerization may be made to progress quantitatively and at the same time a polymer with a chemically convertible functional residue bound to the end may be obtained.

The structure of the iron complex (Y) used in the present invention may be an iron complex with the structure given by general formula (1) below. Quantitative polymerization of the radical polymerizable monomer and production of a R-ATRP polymer may be made possible using the iron complex with this structure.

[Formula 2]

(1)

wherein Fe is trivalent, X is a chlorine atom or bromine atom, $R_1$, $R_2$ and $R_3$ are groups selected from hydrogen atoms, alkyl groups with 1 to 12 carbons and benzyl groups that may have substituent groups of 1 to 8 carbons and m and n are integers from 2 to 3, with m and n all being 2 and $R_1$, $R_2$ or $R_3$ all being groups that are methyl groups or ethyl groups being excluded.

Specific examples of the basic skeleton for the cyclic amine compound in the iron complex given by general formula (1) above include 1,4,7-triazacyclononane (m=n=2), 1,4,7-triazacyclodecane (m=2, n=3), 1,4,8-triazacycloundecane (m=3, n=2) and 1,5,9-triazacyclododecane (m=n=3), but for simple production, 1,4,7-triazacyclononane and 1,5,9-triazacyclododecane backbones are preferable and 1,4,7-triazacyclononane backbones more preferable.

Examples of the alkyl group with 1 to 12 carbons for $R_1$, $R_2$ and $R_3$ in the iron complex given by general formula (1) above include a methyl group, ethyl group, n-propyl group, n-butyl group, isobutyl group, n-pentyl group, n-hexyl group, n-octyl group, n-decyl group and n-dodecyl group.

Examples of the benzyl group that may have a substituent group with 1 to 8 carbons for $R_1$, $R_2$ and $R_3$ in the iron complex given by general formula (1) include a benzyl group, 4-methyl benzyl group, 4-ethyl benzyl group, 4-n-propyl benzyl group, 4-isopropyl benzyl group, 4-n-butyl benzyl group, 4-isobutyl benzyl group, 4-t-butyl benzyl group, 4-methoxybenzyl group, 4-ethoxybenzyl group, 4-n-propoxybenzyl group, 4-isopropoxybenzyl group, 4-n-butoxybenzyl group, 4-isobutoxybenzyl group, 4-t-butoxybenzyl group, 4-trifluoromethyl group.

Examples of the cyclic amine compound in the iron complex shown in general formula (1) above include 1,4-dimethyl-1,4,7-triazacyclononane, 1,4,7-tri-n-propyl-1,4,7-triazacyclononane, 1,4,7-tri-n-butyl-1,4,7-triazacyclononane, 1,4,7-tri-n-pentyl-1,4,7-triazacyclononane, 1,4,7-tri-n-hexyl-1,4,7-triazacyclononane, 1,4,7-tri-n-octyl-1,4,7-triazacyclononane, 1,4,7-tri-n-dodecyl-1,4,7-triazacyclononane, 1,4,7-tribenzyl-1,4,7-triazacyclononane, 1,4,7-tris(4-methylbenzyl)-1,4,7-triazacyclononane, 1,4,7-tris(4-n-butylbenzyl)-1,4,7-triazacyclononane, 1,4,7-tris(4-t-butylbenzyl)-1,4,7-triazacyclononane, 1,4,7-tris(4-methoxybenzyl)-1,4,7-triazacyclononane, 1,4,7-tris(4-butoxybenzyl)-1,4,7-triazacyclononane, 1,4,7-tris(4-octyloxybenzyl)-1,4,7-triazacyclononane, 1,4,7-tris(4-trifluoromethyl)-1,4,7-triazacyclononane, 1-benzyl-4,7-dimethyl-1,4,7-triazacyclononane, 1-benzyl-4,7-diethyl-1,4,7-triazacyclononane, 1,4,7-trimethyl-1,4,7-triazacyclodecane, 1,4,7-triethyl-1,4,7-triazacyclodecane, 1,4,7-tri-n-butyl-1,4,7-triazacyclodecane, 1,4,7-tribenzyl-1,4,7-triazacyclodecane, 1,4,7-tris(4-methylbenzyl)-1,4,7-triazacyclodecane, 1,4,7-tris(4-methoxybenzyl)-1,4,7-triazacyclodecane, 1,4,7-tris(4-trifluoromethyl)-1,4,7-triazacyclodecane, 1,4,8-trimethyl-1,4,8-triazacycloundecane, 1,4,8-triethyl-1,4,8-triazacycloundecane, 1,4,8-tri-n-butyl-1,4,8-triazacycloundecane, 1,4,8-tribenzyl-1,4,8-triazacycloundecane, 1,4,8-tris(4-methylbenzyl)-1,4,8-triazacycloundecane, 1,4,8-tris(4-methoxybenzyl)-1,4,8-triazacycloundecane, 1,4,8-tris(4-trifluoromethyl)-1,4,8-triazacycloundecane, 1,5,9-trimethyl-1,5,9-triazacyclododecane, 1,5,9-triethyl-1,5,9-triazacyclododecane, 1,5,9-tri-n-butyl-1,5,9-triazacyclododecane, 1,5,9-tribenzyl-1,5,9-triazacyclododecane, 1,5,9-tris(4-methylbenzyl)-1,5,9-triazacyclododecane, 1,5,9-tris(4-methoxybenzyl)-1,5,9-triazacyclododecane, 1,5,9-tris(4-trifluoromethyl)-1,5,9-triazacyclododecane.

For the iron complex (Y) having a cyclic amine compound coordinated to a trivalent iron ion and a halogen group in the vicinity of the iron, a 1,4,7-trimethyl-1,4,7-triazacyclononane.$FeCl_3$ complex may be synthesized from 1,4,7-trimethyl-1,4,7-triazacyclononane and iron (III) chloride hexahydrate as described in the Journal of the American Chemical Society, Vol. 109, 1987, p. 7387. However, as described in Inorganica Chimica Acta, Vol 216, 1994, p. 89, the corresponding triazacyclononane.$FeCl_3$ complex cannot be synthesized from 1,4,7-tributyl-1,4,7-triazacyclononane and iron (III) chloride hexahydrate.

According to the present invention, the iron complex (Y) given by general formula (1) above may be obtained with an excellent yield using anhydrous iron (III) chloride instead of iron (III) chloride hexahydrate. In addition, even if anhydrous iron (III) bromide is used, the iron complex given by general formula (1) may be produced in the same manner. Furthermore, it is preferable to perform the synthesis using a dry solvent with little water content, such as dehydrated ether. An iron complex (Y) with high solubility in polymerizable monomers and organic solvents may be provided by using a synthesis method with this nonaqueous system and increasing the number of carbons in $R_1$, $R_2$, and $R_3$ in general formula (1) above.

As given in the general formula (1) above, the cyclic amine compound coordinates to the trivalent iron ion, and the polymerization of the radical polymerizable monomer progresses quantitatively using R-ATRP by making use of the iron complex (Y) with a halogen group in the vicinity of the iron and a radical generator as the polymerization initiator. Polymers that are chemically convertible at the end, as well as polymers formed using these polymers as macroinitiators after isolation, polymers formed by stepwise addition of monomers and polymers where the block copolymer and other structures are controlled may be obtained by this polymerization.

Specifically, the most salient characteristic when this complex is used is that a polymer where the molecular weight distribution of the polymer from the radical polymerizable monomer is 1.1 to 1.4 is easily obtained by combining the iron complex (Y) and the radical generator. Since a halogen is bound to the terminal of the polymers obtained by this method, these polymers may be used as macroinitiators for ATRP, and these terminals may be changed to other compound residues.

In addition, the iron complex given by general formula (1) may be used and recovered after the polymerization.

The iron complex given by general formula (1) in the present invention may be used effectively in the polymerization of radical polymerizable monomers such as (meth)acrylates, styrenes, acrylamides and vinylpyridines. In addition, R-ATRP using the iron complex described above may easily yield high molecular weight polymers and high molecular weight block copolymers.

If the radical generator in the polymerization reaction using the iron complex given by general formula (1) of the present invention is one normally used in radical polymerization of vinyl monomers, any of them may naturally be used, but examples that are particularly typical among these are organic peroxides such as t-butylperoxy(2-ethylhexanoate), t-butyl peroxybenzoate and other peroxide esters, di-t-butyl peroxide, dicumyl peroxide and other dialkyl peroxides, and 1,1-bis(t-butylperoxy)-3,3,5-trimethylcyclohexane and other peroxyketals, azobisisobutyronitrile, azobis cyclohexanecarbonitrile, 2,2'-azobis(2,4-dimethylvaleronitrile) and other azo compounds.

In addition, water soluble peroxides and water soluble azo compounds may be used as the radical generator. Examples are peroxides such as hydroxy-t-butyl peroxide, ammonium sulfate peroxide, potassium sulfate peroxide and hydrogen peroxide, and VA-046B, VA-057, VA-060, VA-067, VA-086, VA-044, V-50, VA-061, VA-080 and the like, which are azo polymerization initiators. Specifically, useful functional groups derived from the initiator residues may be introduced at one end of the polymer by using water soluble azo initiators.

In addition, active halogen compounds such as alpha-halogenocarbonyl compounds, alpha-halogenocarboxylic acid ester compounds, halogenated sulfonyl compounds, alpha-halogenoalkyl arene compounds or polyhalogenated alkane compounds may be used in combination with these as radical generators. More specifically, 1,1-dichloroacetophenone, 1,1-dichloroacetone, 1,1-dibromoacetophenone, 1,1-dibromoacetone and other carbonyl compounds, or 2-bromo-2-methyl ethyl propionate, 2-bromo-2-methyl anthracenyl methyl propionate, 2-chloro-2,4,4-trimethyl dimethyl tartronate, trichloromethyl acetate, alpha-chlorophenyl ethyl acetate, alpha-bromophenyl ethyl acetate, 1,2-bis(alpha-bromopropionyloxy)ethane and like esters, p-toluene sulfonyl chloride, p-toluene sulfonyl bromide, benzenesulfonic acid chloride benzenesulfonic acid bromide methanesulfonic acid chloride and like halogenated sulfonyls, chloromethyl benzene, bromomethyl benzene, iodomethyl benzene, dichloromethyl benzene, dibromomethyl benzene, 1-phenylethyl chloride, 1-phenylethyl bromide and like alpha-halogenoalkyl arenes, or carbon tetrachloride, carbon tetrabromide and like halogenated alkane compounds may be used in combination therewith.

Star polymers may easily be synthesized with the combined use of compounds having three or more active sites for the radical generator. Examples are polyhalogenoalkyls such as trichloromethyl benzene, tetrakischloromethyl benzene, tetrakisbromomethyl benzene, hexakischloromethyl benzene and hexakisbromomethyl benzene.

The combination of the iron catalyst and radical initiator in the present invention may be applied to radical polymerizable monomers in general. Examples of this polymerizable monomer are (meth)acrylates, (meth)acrylate amides, styrenes, vinylpyridines and the like. More specifically, methyl methacrylate, ethyl methacrylate, butyl methacrylate, t-butyl methacrylate, hexyl methacrylate, cyclohexyl methacrylate, benzyl methacrylate, 2-hydroxyethyl methacrylate, 2-dimethylaminoethyl methacrylate and other methacrylate monomers; methyl acrylate, ethyl acrylate, butyl acrylate, t-butyl acrylate, hexyl acrylate, cyclohexyl acrylate, benzyl acrylate, 2-hydroxyethyl acrylate, 2-dimethylaminoethyl acrylate and other acrylate monomers; N,N-dimethyl acrylamide, N,N-diethyl acrylamide, N-isopropyl acrylamide and other acrylamide monomers; styrene, 2-chloromethylstyrene, 3-chloromethylstyrene, 4-chloromethylstyrene, p-methoxystyrene, p-vinyl benzoic acid ester and other styrene monomers, or p-vinylpyridine, o-vinylpyridine and other vinylpyridine monomers may be used.

In the polymerization according to general formula (1) above of the present invention, these polymerizable monomers alone or two or more of them may used in the reaction at the same time. In addition, two or more radical polymerizable monomers may be added at fixed time intervals in the polymerization reaction. By adding the next radical polymerizable monomer after the first radical polymerizable monomer has been consumed, the polymer obtained may be given a diblock, triblock or greater block copolymer structure. By selecting a polymerizable monomer from styrenes and (meth)acrylates in the synthesis of block copolymers, block copolymers may be obtained from these two polymer backbones. Likewise, block copolymers of styrenes and vinylpyridines, block copolymers of styrenes and acrylamides and block copolymers from (meth)acrylates and acrylamides may be obtained. In addition, amphiphilic block copolymers formed from a hydrophilic polymer backbone and a hydrophobic polymer backbone may be obtained by using a hydrophilic monomer and a hydrophobic monomer. In addition, a double hydrophobic block copolymer may be obtained by polymerization of two hydrophilic monomers.

When the radical generator and the iron complex of general formula (1) above are mixed and the polymerizable monomer described above is polymerized in the present invention, 1 to 6 mol of this iron complex is used per mole of the radical generator, preferably 1.5 to 3 mol.

In addition, if the mole ratio of the radical polymerizable monomer and radical generator is 50 to 8000, presupposing a preferable mole ratio for the radical generator and iron complex described above, polymerization may be carried out in a suitable manner. The number average molecular weight may be increased or decreased by changing the mole ratio of the radical generator and the radical polymerizable monomer. Specifically, it is desirable to set the number of moles of the radical polymerizable monomer high to obtain a polymer or block copolymer with a high number average molecular weight.

When the polymerization reaction is carried out using the iron complex shown in general formula (1) of the present invention above, the reaction may be carried out at a reaction temperature of room temperature or above, preferably 30 to 130° C.

It is desirable to set the reaction time according to the type of catalytic system, type of radical polymerizable monomer and reaction temperature. Furthermore, it is desirable to set the reaction time to match the molecular weight control for the polymer being obtained.

The polymerization reaction of the present invention is applicable to different polymerization methods such as bulk polymerization without solvents, solution polymerization in the presence of a solvent, or polymerization in the presence of alcohols or an aqueous medium.

Solvents usable in polymerization reactions that use the metal complex of general formula (1) of the present invention above include dichloromethane, 1,2-dichloroethane, tetrahydrofuran, acetonitrile, benzene, toluene, chlorobenzene, dichlorobenzene, anisole, cyanobenzene, dimethylformamide, N,N-dimethylacetamide, methyl ethyl ketone, acetone, methanol, ethanol, propanol, butanol, pentanol, hexanol, and the like. In addition, the polymerization reaction may be carried out in water and an aqueous solvent obtained by mixing water and an organic solvent that dissolves with water.

In polymerization using the iron complex given by general formula (1) above in the present invention, the polymer is precipitated by itself after that polymerization reaction is complete by an operation where precipitation of the reaction liquid is carried out in a solvent such as an alcohol, acetone, an ether, water or the like. The iron complex may be dissolved in these solvents. Therefore, the iron complex is eliminated from the polymer that is obtained, and the iron complex in the solvent may be recovered by concentration.

An organic solvent alone or a mixed solvent of an organic solvent and water may be suitable for use as the solution for recovering a catalyst described above.

In the production method of the present invention, environmental contamination may be controlled more than toxic metal ion systems such as copper complexes by using the iron complex given by general formula (1) above, and in addition, the post-processing processes for the polymer obtained may be simplified.

In addition, by using the iron complex given by general formula (1) above and a radical initiator in the production method of the present invention, the polymerization reaction system becomes extremely simple and does not need other ligands. Furthermore, because of the superior catalytic activity of the iron complex, the radical polymerization reaction thereof progresses quantitatively. In addition, since an active terminus that is not obtained with normal radical polymerization is formed on the polymer that is obtained, a block copolymer may be produced simply by adding another radical polymerizable monomer after the quantitative polymerization.

The polymers and block copolymers obtained from this production method of the present invention may be used broadly for various applications, such as ink, pigment dispersants, color filters, films, coatings, molding materials, adhesives, electrical and electronic component materials and medical materials.

The present invention is described in more detail in the following Examples. However, the present invention is not limited to the Examples, which are provided for illustration purposes only and in no way limit the scope of the invention.

EXAMPLES

The present invention will be described in more detail using the following examples and comparative examples.

The measurements in the examples were carried out by the following methods.

(GPC Measurement Method)

Measurements were made using a Waters GPC 600 control system (RI detector: 610 differential refractometer system), Shodex GPC KF-800 series GPC columns (KF-802×2+KF-803×1+KF-804×1), THF for the eluting solution with a flow rate of 1.0 mL/min and temperature adjusted to 40° C.

(NMR Measurements)

$^1$H-NMR measurements were carried out with a JEOL Ltd. Lambda 300.

(Single Crystal X-ray Structure Analysis)

Single crystal x-ray structure analysis was carried out using a RASA 5R (Rigaku Corp.) single crystal x-ray structure analysis system.

Example 1

Synthesis of Iron Complex 1

Figure 1:
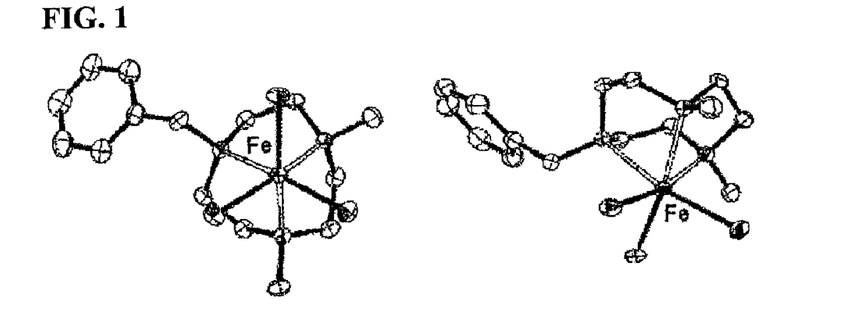
FIG. 1 is a single crystal x-ray structure analysis of iron complex 1.

178 mg (1.1 mmol) of anhydrous $FeCl_3$ and 40 mL of anhydrous diethyl ether were added to a 100 mL Schrenck tube in an argon atmosphere. After they were completely dissolved, a 10 mL anhydrous diethyl ether solution of 247 mg (1.0 mmol) of 1-benzyl-4,7-dimethyl-1,4,7-triazacyclononane synthesized according to the method described on p. 189 of Inorganica Chimica Acta Vol. 295, 1999, was dripped in slowly at room temperature. After mixing for one hour, a crude product containing complex 1 was separated out by filtration. After this solid was heated and dissolved in 50 mL of acetonitrile and the undissolved material eliminated by filtration, the filtrate was concentrated, and a bright yellow iron complex 1 (Formula 3) was obtained (Yield: 323 mg, 94%). The structure of the complex was confirmed using single crystal x-ray structure analysis. It is shown in FIG. 1.

[Formula 3]

Example 2

Synthesis of Iron Complex 2

Figure 2:
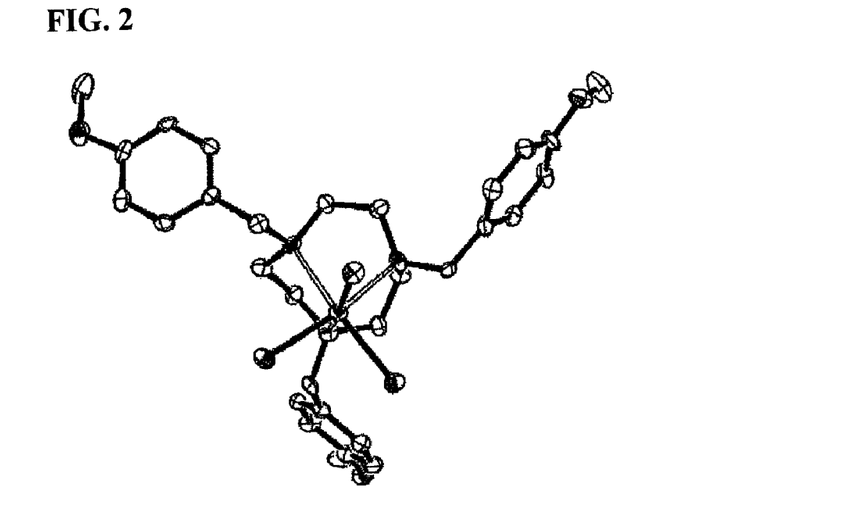
FIG. 2 is a single crystal x-ray structure analysis of iron complex 2.

422 mg (2.6 mmol) of anhydrous $FeCl_3$ and 80 mL of anhydrous diethyl ether were added to a 100 mL Schrenck tube in an argon atmosphere. After they were completely dissolved, a 15 mL anhydrous diethyl ether solution of 978 mg (2.0 mmol) of 1,4,7-tris(4-methoxybenzyl)-1,4,7-triazacyclononane synthesized according to the method described on p. 11575 of the Journal of the American Chemical Society Vol. 118, 1996, was dripped in slowly at room temperature. After mixing for one hour, a crude product containing complex 2 was separated out by filtration. After this solid was dissolved in 130 mL of methylene chloride and the undissolved material eliminated by filtration, the filtrate was concentrated, and a bright yellow iron complex 2 (Formula 4) was obtained. (Yield: 1.22 g, 94%). The structure of the complex was confirmed using single crystal x-ray structure analysis. It is shown in FIG. 2.

Example 3

Synthesis of Iron Complex 3

162 mg (1.0 mmol) of anhydrous FeCl₃ and 40 mL of anhydrous diethyl ether were added to a 100 mL Schrenck tube in an argon atmosphere. After they were completely dissolved, a 10 mL anhydrous diethyl ether solution of 533 mg (1.33 mmol) of 1,4,7-tribenzyl-1,4,7-triazacyclononane synthesized according to the method described on p. 491 of Organometallics Vol. 15, 1996, was dripped in slowly at room temperature. After mixing for one hour, a crude product containing complex 3 was separated out by filtration. After this solid was dissolved in 100 mL of methylene chloride and the undissolved material eliminated by filtration, the filtrate was concentrated, and a yellow iron complex 3 (Formula 5) was obtained (Yield: 533 mg, 95%).

[Formula 5]

The results of using FeCl₃.6H₂O instead of FeCl₃ are shown in the following comparative example.

Comparative Example 1

300 mg (1.1 mmol) of anhydrous FeCl₃.6H₂O and 40 mL of anhydrous diethyl ether were added to a 100 mL Schrenck tube in an argon atmosphere. After they were completely dissolved, a 10 mL anhydrous diethyl ether solution of 400 mg (1.0 mmol) of 1,4,7-tribenzyl-1,4,7-triazacyclononane was dripped in slowly at room temperature. After mixing for two hours, a crude product containing complex 3 was separated out by filtration. This solid was washed with 200 mL of methanol, and a yellow iron complex 3 was obtained as undissolved material. (Yield: 160 mg, 29%).

Example 4

Synthesis of Iron Complex 4

Figure 3:
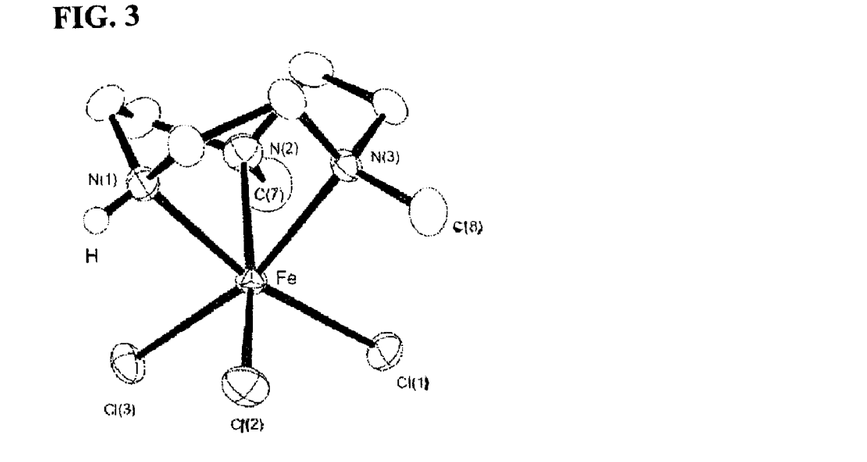
FIG. 3 is a single crystal x-ray structure analysis of iron complex 4.

211 mg (1.3 mmol) of anhydrous FeCl₃ and 40 mL of anhydrous diethyl ether were added to a 100 mL Schrenck tube in an argon atmosphere. After they were completely dissolved, a 10 mL anhydrous diethyl ether solution of 157 mg (1.0 mmol) of 1,4,-dimethyl-1,4,7-triazacyclononane synthesized according to the method described on p. 60 of Zeitschrift für anorganische and allgemeine Chemie No. 608, 1998, was dripped in slowly at room temperature. After mixing for one hour, a crude product containing complex 4 was separated out by filtration. After this solid was heated and dissolved in 70 mL of acetonitrile and the undissolved material eliminated by filtration, the orange solution was concentrated, and an orange iron complex 4 (Formula 6) was obtained (Yield: 297 mg, 93%). The structure of the complex was confirmed using single crystal x-ray structure analysis.

It is shown in FIG. 3.

[Formula 6]

Example 5

Synthesis of Complex 5

Other than using 213 mg (1.0 mmol) of 15,9-trimethyl-15,9-triazacyclododecane synthesized according to the method described on page 7755 of Tetrahedron Letters Vol. 32, No. 52, 1991 instead of 1,4,-dimethyl-1,4,7-triazacyclononane, this was carried out according to Example 4. Complex 5 (Formula 7): brown solid (yield: 260 mg, 70%).

[Formula 7]

Example 6

Synthesis of Iron Complex 6

Other than using 298 mg (1.0 mmol) of 1,4,7-tri-n-butyl-1,4,7-triazacyclononane synthesized according to the method described on page 1986 of Macromolecules Vol. 33, 2000 instead of 1,4,-dimethyl-1,4,7-triazacyclononane, this was carried out according to Example 4. Complex 6 (Formula 8): yellow solid (yield: 412 mg, 90%).

[Formula 8]

Example 7

Synthesis of 1,4,7-tri-n-octyl-1,4,7-triazacyclononane

Triazacyclononane (1.0 g, 7.74 mmol), triethylamine (5.1 g, 50 mmol) and anhydrous methylene chloride (100 mL) were added to a 200 mL three neck flask provided with a dripping funnel in an argon atmosphere. n-octanoic acid chloride (4.2 g, 25.8 mmol) was added to this mixture by the dripping funnel at room temperature, and the reaction mixture was stirred for two days at room temperature. This reaction mixture was washed with water (25 mL×4), and next, the organic layer obtained was dried using anhydrous magnesium sulfate. After concentration, there was formation using silica gel column chromatography, and 1,4,7-tri(n-heptylcarbonyl)-1,4,7-triazacyclononane (3.14 g, 80% yield) was obtained.

All of the 1,4,7-tri(n-heptylcarbonyl)-1,4,7-triazacyclononane was put into a 200 mL three neck flask provided with a reflux tube in an argon atmosphere, and a $BH_3.THF$ solution (100 mmol, 100 mL) was added thereto and reflowed for one night. To break down the excess $BH_3.THF$, methanol was added slowly to the reaction mixture after allowing it to cool to room temperature, and after concentration, this was dissolved in 1-butanol (50 mL), water (50 mL) and concentrated hydrochloric acid (100 mL and reflowed for one night. The reaction mixture obtained was cooled in an ice bath, and a 48% aqueous solution of sodium hydroxide was added until the pH exceeded 12. After amine separation, this aqueous solution was extracted in methylene chloride (8×50 mL). After the organic layer that was obtained was dried using anhydrous sodium sulfate, it was concentrated, and pale yellow, oily 1,4,7-tri-n-octyl-1,4,7-triazacyclononane (2.45 g, 85% yield) was obtained.

Synthesis of Iron Complex 7

Other than using 466 mg (1.0 mmol) of 1,4,7-tri-n-octyl-1,4,7-triazacyclononane instead of 1,4,-dimethyl-1,4,7-triazacyclononane, this was carried out according to Example 4. Complex 7 (Formula 9): yellow solid (yield: 577 mg, 92%).

[Formula 9]

Example 8

Synthesis of 1,4,7-tri-n-dodecyl-1,4,7-triazacyclononane

Other than using 3.87 mg (5.7 mmol) of 1,4,7-trilauroyl-1,4,7-triazacyclononane synthesized according to the method described on page 4630 of Langmuir Vol. 10, 1994 instead of 1,4,7-tri(n-heptylcarbonyl)-1,4,7-triazacyclononane, this was carried out according to Example 7, and 1,4,7-tri-n-dodecyl-1,4,7-triazacyclononane was synthesized (2.96 g, 82%).

Synthesis of Iron Complex 8

Other than using 634 mg (1.0 mmol) of 1,4,7-tri-n-dodecyl-1,4,7-triazacyclononane instead of 1,4-dimethyl-1,4,7-triazacyclononane, this was carried out according to Example 4. Complex 8 (Formula 10): yellow solid (yield: 733 mg, 92%).

[Formula 10]

Example 9

Synthesis of 1,4,7-tris(4-n-octyloxybenzyl)-1,4,7-triazacyclononane Other than using 6.94 g (25.8 mmol of (4-n-octyloxy)benzoyl chloride instead of n-octanoic acid chloride this was carried out according to Example 7, and 1,4,7-tris(4-n-octyloxybenzyl)-1,4,7-triazacyclononane (2.96 g, 64%) was synthesized.

Synthesis of Iron Complex 9

Other than using 784 mg (1.0 mmol) of 1,4,7-tris(4-n-octyloxybenzyl)-1,4,7-triazacyclononane instead of 1,4-dimethyl-1,4,7-triazacyclononane, this was carried out according to Example 4. Complex 9 (Formula II): yellow solid (yield: 861 mg, 91%).

[Formula 11]

Example 10

A stirrer, iron complex 1 (41 mg, 0.1 mmol) and AIBN (8.2 mg, 0.05 mmol) were put into a test tube in an argon atmosphere, and methyl methacrylate (2.0 g, 20 mmol) and 2 mL of acetonitrile were added. The vessel was sealed and stirred for 14 hours 80° C. The conversion rate at this time was 94%. The reaction mixture was diluted with 7 mL of THF, and dripped into 140 mL of stirred methanol. The polymeric substance was separated by filtration, and drying was carried out under reduced pressure (yield: 1.79 g). The PMMA obtained had Mn=29300 and Mw/Mn=1.35.

Example 11

Other than using iron complex 4 (32 mg, 0.1 mmol) instead of complex 1, this was carried out in the same manner as Example 10. The conversion rate was 98%, and the reaction mixture had Mn=32600 and Mw/Mn=1.49.

Example 12

Other than using iron complex 5 (38 mg, 0.1 mmol) instead of complex 1, this was carried out in the same manner as Example 10. The conversion rate was 90%, and the reaction mixture had Mn=28500 and Mw/Mn=1.38.

Example 13

A stirrer, iron complex 3 (56 mg, 0.1 mmol) and azobis cyclohexanecarbonitrile (12.2 mg, 0.05 mmol) were put into a test tube in an argon atmosphere, and styrene monomer (2.08 g, 20 mmol) was added. The vessel was sealed and stirred for 14 hours 1200° C. The conversion rate was 98%, and the reaction mixture was diluted with 7 mL of THF, and dripped into 140 mL of stirred methanol.

The polymeric substance was separated by filtration, and drying was carried out under reduced pressure (yield: 1.98 g). The polystyrene obtained had Mn=23800 and Mw/Mn=1.45.

Comparative Example 2

Other than not adding iron complex 2, polymerization was carried out under the same conditions as Example 13 above. As a result, 1.75 g of polymer was obtained (conversion rate: 80%, Mn=44600, Mw/Mn=2.78). From this it is clear that in systems where the complex is not added, the molecular weight distribution expands, and the contribution of iron complex 2 to the polymerization is clear.

Example 14

Iron complex 2 (1.30 g, and 2 mmol), azobis cyclohexanecarbonitrile (224 mg, 1 mmol) and styrene monomer (10.4 g, 0.1 mol) were put into a reaction vessel in an argon atmosphere and stirred for eight hours at 120° C. The conversion rate at this time was 84%, and the polystyrene produced had Mn=5200 and Mw/Mn=1.13.

Example 15

A stirrer, iron complex 2 (65 mg, 0.1 mmol) and azobis cyclohexanecarbonitrile (12.2 mg, 0.05 mmol) were put into a test tube in an argon atmosphere, and styrene monomer (2.08 g, 20 mmol) was added. The vessel was sealed and stirred for 17 hours 130° C. The conversion rate was 99%, and the reaction mixture had Mn=22600 and Mw/Mn=1.26.

Example 16

A stirrer, iron complex 2 (65 mg, 0.1 mmol) and azobis cyclohexanecarbonitrile (12.2 mg, 0.05 mmol) were put into a test tube in an argon atmosphere, and styrene monomer (2.08 g, 20 mmol) and 2 mL of mesitylene were added. The vessel was sealed and stirred for 40 hours 120° C. The conversion rate was 88%, and the reaction mixture had Mn=19500 and Mw/Mn=1.27.

Example 17

A stirrer, iron complex 2 (65 mg, 0.1 mmol) and azobis cyclohexanecarbonitrile (12.2 mg, 0.05 mmol) were put into a test tube in an argon atmosphere, and butyl acrylate (2.56 g, 20 mmol) and 2 mL of cyclohexanone were added. The vessel was sealed and stirred for 20 hours 120° C. The conversion rate was 66%, and the reaction mixture had Mn=13400 and Mw/Mn=1.69.

Example 18

Block Copolymerization of Ethyl Acrylate and Phenoxyethyl Methacrylate

Iron complex 2 (326 mg, 0.5 mmol), AIBN (41 mg, 0.25 mmol), ethyl acrylate (5 g, 50 mmol), phenoxyethyl methacrylate (10.3 g, 50 mmol) and 15 mL of acetonitrile were put into a reaction vessel in an argon atmosphere and stirred for 20 hours at 80° C. The conversion rates for the ethyl acrylate and phenoxyethyl methacrylate at this time were 67% and 94%, respectively. The polymeric substance produced had Mn=27900 and Mw/Mn=1.93. When the polymeric substance obtained was analyzed by $^1$H-NMR (600 MHz, CDCl3), it was found that there was random copolymeric substance of ethyl acrylate and phenoxyethyl methacrylate.

Example 19

Block Copolymerization of Styrene Monomer and Methyl Methacrylate

Figure 4:
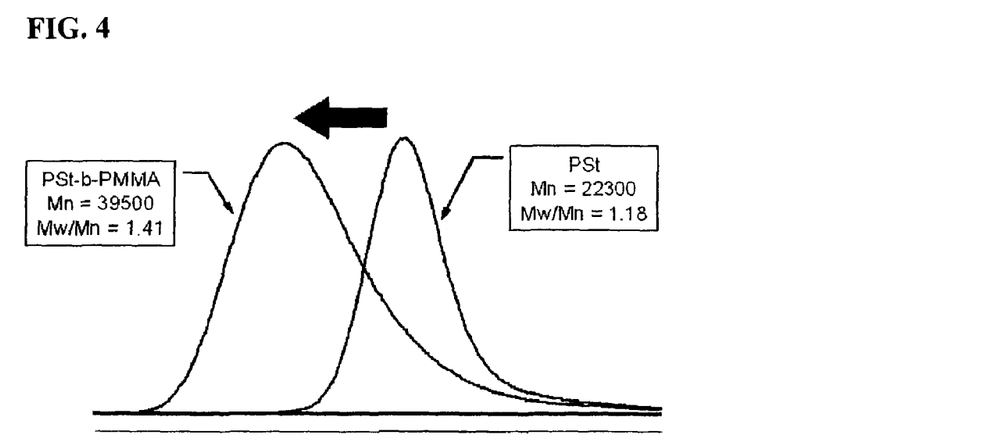
FIG. 4 is a GPC chart for the polymer before and after block copolymerization in Example 19.

Iron complex 2 (652 mg, and 1 mmol), azobis cyclohexanecarbonitrile (122 mg, 0.5 mmol) and styrene monomer (20.8 g, 0.2 mol) were put into a reaction vessel in an argon atmosphere and stirred for 23 hours at 120° C. The conversion rate at this time was 88%, and the polystyrene produced had Mn=22300 and Mw/Mn=1.18. Next, after a mixture of methyl methacrylate (20 g, 0.2 mol) and 20 mL of acetonitrile were added to the reaction mixture at 60° C., it was further reacted for 17 hours at 95° C. The conversion rate for the methyl methacrylate at this time was 68%, and the polymer produced had Mn=39500 and Mw/Mn=1.41. FIG. 4 is a GPC chart for the polymer before and after block copolymerization. As a result of the progress of the block copolymerization, the polymer shifted greatly to the high molecular weight side.

Example 20

Figure 5:
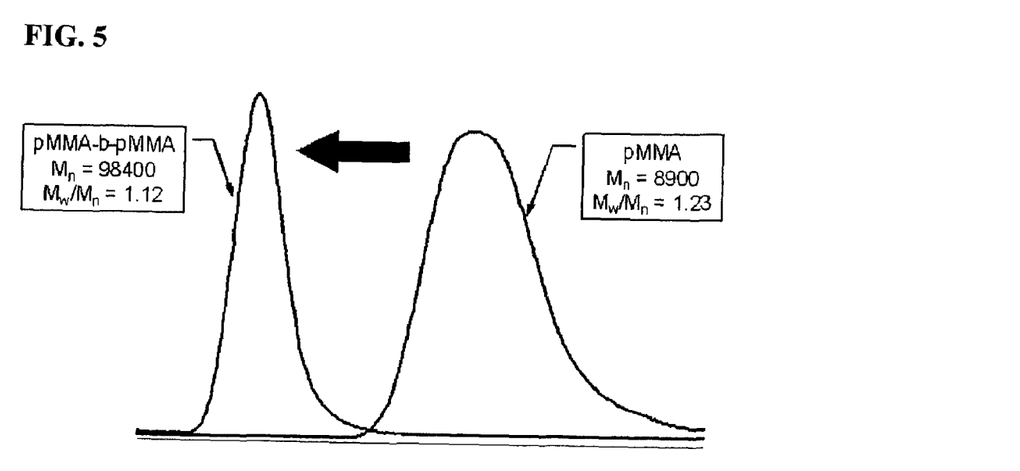
FIG. 5 is the GPC chart when methyl methacrylate is added stepwise in Example 20.

Molecular Weight Control of Polymers Using Polymerization by Stepwise Addition of Monomers Iron complex 2 (1.30 g, 2 mmol), dimethyl 2,2'-azobis (isobutyrate) (231 mg, and 1 mmol), methyl methacrylate (10 g, 0.1 mol) and acetonitrile (10 mL) were put into a reaction vessel in an argon atmosphere and stirred for 19 hours at 80° C. The conversion rate at this time was 99%, and the polymethyl methacrylate produced had Mn=8900 and Mw/Mn=1.23. Next, after methyl methacrylate (80 g, 0.8 mol) was added to the reaction mixture at 60° C., it was further reacted for 22 hours at 80° C. The conversion rate for the methyl methacrylate at this time was 71%, and the polymer produced had Mn=98400 and Mw/Mn=1.12. FIG. 5 is the GPC chart for the polymer before and after post-polymerization. As a result of the progress of the post-polymerization, the polymer shifted greatly to the high molecular weight side.

Example 21

Test of Catalyst Recovery (Polymerization Reaction)

A stirrer, iron complex 2 (65 mg, 0.1 mmol) and azobis cyclohexanecarbonitrile (12.2 mg, 0.05 mmol) were put into a test tube in an argon atmosphere, and styrene monomer (2.08 g, 20 mmol) was added. The vessel was sealed and stirred for 12 hours 120° C. The conversion rate was 86%, and the polystyrene produced had Mn=21000 and Mw/Mn=1.20.

[Separation and Recovery of Polymer and Catalyst]

The polymer that was synthesized with the first polymerization above was dissolved in 7 mL of THF and reprecipitated and purified by dripping into 140 mL of methanol. When the polymer that was precipitated and the solution part that included the catalyst were each dried under reduced pressure, 1.73 g of a substantially colorless pure polymer and 100 mg of a yellow solid from the solution part containing the catalyst were recovered.

INDUSTRIAL APPLICABILITY

The novel iron complex having a cyclic amine compound as a ligand that is obtained according to the present invention may be used for producing polymers by polymerizing a radical polymerizable monomer in the presence of the iron complex and a radical generator.

Patents, patent applications and non-patent publications cited in this application are hereby incorporated by reference in their entirety.

The invention claimed is:

1. An iron complex given by general formula (1)

[Formula 1]

(1)

wherein Fe is trivalent, X is a chlorine atom or bromine atom, $R_1$, $R_2$ and $R_3$ are groups selected from hydrogen atoms or benzyl groups that optionally have substituent groups with 1 to 8 carbons and m and n are integers from 2 to 3, wherein if m and n each is 2, then each of $R_1$, $R_2$, and $R_3$ is not hydrogen.

2. The iron complex according to claim 1 wherein $R_1$, $R_2$ or $R_3$ in said general formula (1) is a benzyl group having a substituent with 1 to 8 carbons in the fourth position in the benzene ring.

3. The iron complex according to claim 2 wherein said substituent is an alkyl group with 1 to 8 carbons, an alkoxy group with 1 to 8 carbons or a fluorinated alkyl group with 1 to 8 carbons.

4. A production method for the iron complex given by general formula (1)

[Formula 1]

(1)

comprising reacting a cyclic amine compound given by general formula (2) with anhydrous iron (III) chloride or anhydrous iron (III) bromide

[Formula 2]

(2)

wherein $R_1$, $R_2$ and $R_3$ are groups selected from hydrogen atoms or benzyl groups that optionally have substituent groups with 1 to 8 carbons and m and n are integers from 2 to 3, wherein if m and n each is 2, then each of $R_1$, $R_2$, and $R_3$ is not hydrogen.

5. A production method for a polymer such that the iron complex according to claim 1 is used as a polymerization catalyst and at least one radical polymerizable monomer is polymerized in the presence of a radical polymerization initiator.

6. The production method for a polymer according to claim 5 wherein said radical polymerization initiator is at least one radical polymerization initiator selected from the group consisting of peroxides and azo compounds.

7. The production method for a polymer according to claim 6 wherein at least one radical generator is selected from the group consisting of alpha-halogenocarbonyl compounds, alpha-halogenocarboxylic acid esters, halogen methylarenes and polyhalogenated alkanes is further used in combination therewith.

8. The production method for a polymer according to claim 5 wherein said radical polymerizable monomer is at least one radical polymerizable monomer selected from the group consisting of styrene monomers, vinylpyridine monomers, (meth)acrylate ester monomers and (meth)acrylamide monomers.

9. The production method for a polymer according to claim 5 wherein block copolymerization is carried out using two or more radical polymerizable monomers for said radical polymerizable monomer.

10. The production method for a polymer according to claim 5 wherein polymerization is carried out in an aqueous medium.

11. The production method for a polymer according to claim 5 wherein polymerization is carried out without a medium.

12. The production method of claim 5 wherein the polymer is washed using at least one of water or a water soluble organic solvent and the iron complex is recovered.

* * * * *